United States Patent [19]

Chetcuti

[11] Patent Number: 5,378,744
[45] Date of Patent: Jan. 3, 1995

[54] SYNTHETIC POLYMER COMPOSITIONS CONTAINING CHARGE TRANSFER COMPLEXES, THEIR PREPARATION AND THE USE THEREOF

[75] Inventor: Peter Chetcuti, Basel, Switzerland

[73] Assignee: Ciba-Geigy Corporation, Ardsley, N.Y.

[21] Appl. No.: 7,426

[22] Filed: Jan. 22, 1993

[30] Foreign Application Priority Data

Jan. 29, 1992 [CH] Switzerland .................. 242/92-1

[51] Int. Cl.$^6$ .............. C08K 5/3415; C08K 5/3417; C08K 5/45; C08K 5/48
[52] U.S. Cl. .................. 524/84; 524/83; 524/94; 524/108; 524/109; 524/111
[58] Field of Search ............ 524/84, 206, 83, 94, 524/108, 109, 111

[56] References Cited

U.S. PATENT DOCUMENTS

| | | | |
|---|---|---|---|
| 4,578,220 | 3/1986 | Huenig et al. | 260/239 |
| 4,981,962 | 1/1991 | Baumann et al. | 540/1 |
| 5,001,243 | 3/1991 | Fischer et al. | 552/201 |
| 5,009,812 | 4/1991 | Finter et al. | 252/500 |
| 5,011,944 | 4/1991 | Kvita et al. | 549/214 |
| 5,108,841 | 4/1992 | Wegmann et al. | 428/411.1 |
| 5,112,977 | 5/1992 | Fischer et al. | 546/195 |
| 5,153,321 | 10/1992 | Finter et al. | 540/1 |
| 5,158,829 | 10/1992 | Wegmann et al. | 428/411.1 |

FOREIGN PATENT DOCUMENTS

| | | |
|---|---|---|
| 285564 | 10/1988 | European Pat. Off. |
| 344109 | 11/1989 | European Pat. Off. |
| 3437814 | 10/1983 | Germany |

OTHER PUBLICATIONS

Synthetic Metals, 41–43 (1991) pp. 2365–2375 Stanton Rak et al.

*Primary Examiner*—Kriellion S. Morgan
*Attorney, Agent, or Firm*—George R. Dohmann

[57] ABSTRACT

A composition comprising a) a thermosetting, thermoplastic or structurally crosslinked polymer and b) a charge transfer complex of formula I in the form of a network of crystal needles in the polymer matrix $$[A]^{\ominus} \cdot B^{\oplus} \quad (I),$$

wherein A is a compound of formula II or a mixture of compounds of formula II

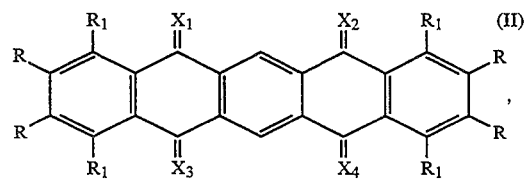

wherein the R substituents are identical and are H or $C_1$-$C_4$alkyl, or the adjacent R substituents, taken together, are —$(CH_2)_3$— or —$(CH_2)_4$—; $R_1$ or $C_1$-$C_4$ alkyl; and $H_1$ is =N—CN, and $X_2$, $X_3$ and $X_4$ are each independently of one another =O or =N—CN, and B is a compound of formula III or IIIa

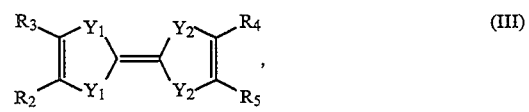

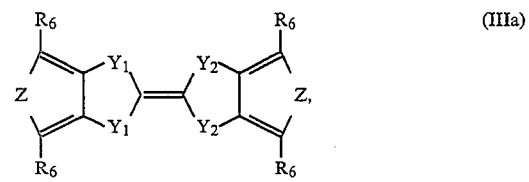

wherein $R_2$, $R_3$, $R_4$ and $R_5$ are each independently of one another H, linear or branched $C_1$-$C_{18}$-alkyl-$(Z_1)_n$—, phenyl-$(Z_1)_n$- or benzyl-$(Z_1)_n$—which are unsubstituted or substituted by $C_1$-$C_4$alkyl, $C_1$-$C_4$alkyl, $C_1$-$C_4$alkoxy or $C_1$-$C_4$alkylthio, or $R_2$ and $R_3$ as well as $R_4$ and $R_5$ are together, each independently of the other, trimethylene, tetramethylene, —$Z_2$—$(CH_2)$—$Z_2$—, —$Z_2$—$(CH_2)_2$—$Z_2$—, —$Z_1$—CH=CH—$Z_1$—or —CH=CH—CH=CH—, each unsubstituted or substi- (Abstract continued on next page.)

tuted by $C_1$–$C_4$alkyl, $C_1$–$C_4$alkoxy or $C_1$–$C_4$alkylthio, n is 0 or 1 steht, $Y_1$ and $Y_2$ are each independently of the other —S— or —Se—, $Z_1$ is —S— or —Se—, $Z_2$ is —O—, —S— or —Se—, Z is —S—, —Se— or $NR_7$, and $R_7$ is H, $C_1$–$C_6$alkyl, phenyl or benzyl, and $R_6$ is H, $C_1$–$C_4$alkyl, phenyl or benzyl. The composition is an electric conductor.

27 Claims, No Drawings

SYNTHETIC POLYMER COMPOSITIONS CONTAINING CHARGE TRANSFER COMPLEXES, THEIR PREPARATION AND THE USE THEREOF

SYNTHETIC POLYMER COMPOSITIONS CONTAINING CHARGE TRANSFER COMPLEXES, THEIR PREPARATION AND THE USE THEREOF

The present invention relates to compositions comprising a synthetic polymer and a charge transfer complex (hereinafter abbreviated to CT complex) of pentacenecyanoimine derivatives as electron acceptors and chalcogenated fulvalenes as electron donors; to a process for their preparation; and to the use of said compositions as electric conductors, conveniently for making electrically conductive films, foils or coatings. These CT complexes are radical cation salts.

Powdered CT complexes comprising tetra-substituted pentacenecyanoimine and tetrathiofulvalene as electron donors and having a conductivity of about 6 S/cm are described in Synthetic Metals, 41–43, pages 2365–2375 (1991). However, powdered materials are insufficiently able to enhance the conductivity of polymer materials, as after processing the particles are encapsulated by the polymer material and therefore insulated.

U.S. Pat. No. 5,009,812 discloses antistatically treated and conductive polymers that contain e.g. CT complexes of tetrathio-, tetraseleno- or tetratellurotetracenes as electron donors and halogens or oxygen as electron acceptors. In these materials the CT complexes form needle networks in the polymer matrix. The preparation of these conductive polymers necessitates the use of reagents that cause corrosion in metallic machine pans, so that special measures have to be taken to protect the machines. In addition, the poor solubility of chalcogenic tetracenes makes rather high temperatures necessary for the preparation of the polymers. This is regarded as uneconomic and also requires industrial hygiene measures owing to the too high volatility of the reagants used. In addition, the use of tetraseleno- and tetratellurotetracenes is considered questionable for toxicological reasons.

Surprisingly, it has been found that pentacenecyanoimines and specific fulvalene derivatives form CT complexes which, unexpectedly, even in the presence of binders, crystallise in needle form, have a high conductivity and exert virtually no corrosive action on the metallic pans of processing machines. The starting compounds are also soluble in less polar organic solvents so that no very high temperatures are required for the preparation of the CT complexes. The CT complexes have superior stability to moisture and heat.

In one of its aspects, the invention relates to a composition comprising a) a thermosetting, thermoplastic or structurally crosslinked polymer and b) a charge transfer complex of formula I in the form of a network of crystal needles in the polymer matrix $$[A]^{\ominus} \cdot B^{\oplus} \qquad (I),$$

wherein A is a compound of formula II or a mixture of compounds of formula II

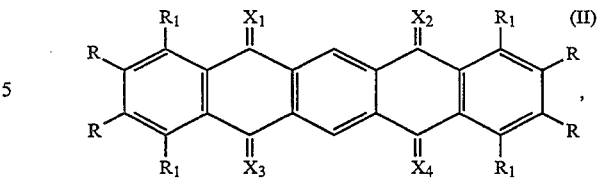

wherein the R substituents are identical and are H or $C_1$–$C_4$alkyl, or the adjacent R substituents, taken together, are —(CH$_2$)$_3$— or —(CH$_2$)$_4$; $R_1$ is H or $C_1$–$C_4$ alkyl; and $X_1$ is =N—CN, and $X_2$, $X_3$ and $X_4$ are each independently of one another =O or =N—CN, and B is a compound of formula III or IIIa

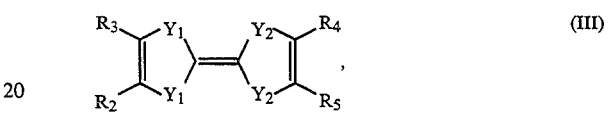

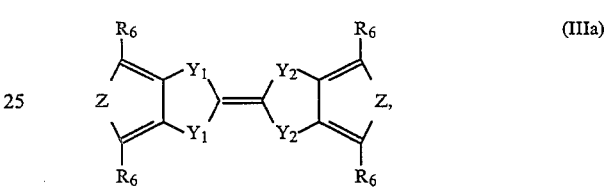

wherein $R_2$, $R_3$, $R_4$, and $R_5$ are each independently of one another H, linear or branched $C_1$–$C_{18}$alkyl-$(Z_1)_n$—, phenyl-$(Z_1)_n$—or benzyl-$(Z_1)_n$-which are unsubstituted or substituted by $C_1$–$C_4$alkyl, $C_1$–$C_4$alkoxy or $C_1$–$C_4$alkylthio, or $R_2$ and $R_3$ as well as $R_4$ and $R_5$ are together, each independently of the other, trimethylene, tetramethylene, —$Z_2$—(CH$_2$)—$Z_2$—, —$Z_2$—(CH$_2$)$_2$—$Z_2$—, —$Z_1$—CH=CH—$Z_1$—or —CH=CH—CH=CH—, each unsubstituted or substituted by $C_1$–$C_4$alkyl, $C_1$–$C_4$alkylthio, n is 0 or 1 steht, $Y_1$ and $Y_2$ are each independently of the other —S—or —Se—, $Z_1$ is —S—or —Se—, $Z_2$ is —O—, —S—or —Se—, Z is —S—, —Se—or NR$_7$, and R$_7$ is H, $C_1$–$C_6$alkyl, phenyl or benzyl, and R$_6$ is H, $C_1$–$C_4$alkyl, phenyl or benzyl.

R and $R_1$ defined as alkyl may be methyl, ethyl, n- or isopropyl or n-, iso- or tert-butyl. Preferred alkyl radicals are methyl and ethyl. In a preferred embodiment of the invention, the R substituents are $C_1$–$C_4$alkyl and the $R_1$ substituents are H, or the $R_1$ substituents are $C_1$–$C_4$alkyl and the R substituents are H. Preferably R and $R_1$ are H, methyl or ethyl. In a particularly preferred embodiment of the invention, R and $R_1$ are H.

In another preferred embodiment of the invention, $X_1$ and $X_4$ are =N—CN and $X_2$ and $X_3$ are =O or =N—CN, or $X_2$ and $X_3$ are =N—CN and $X_1$ and $X_4$ are =O or =N—CN. The most preferred meaning of $X_1$, $X_2$, $X_3$, and $X_4$ is =N—CN.

The compound of formula II is preferably 5,7,12,14-pentacenetetracyanoimine which is in pure form or contains up to 10 % by weight, based on the total composition, of compounds of formula II in which one or two cyanoimine groups are replaced by oxygen.

The compounds of formulae III and IIIa preferably have a reduction potential of less than or equal to 0.44 V, based on the standard calomel electrode.

In the compounds of formula III, $R_2$ and $R_3$ and $R_4$ and $R_5$ are preferably identical and, most preferably, $R_2$ to $R_5$ are identical.

In a preferred embodiment of the invention, $Y_1$ and $Y_2$ in the compounds of formulae III and IIIa are either —S— or —Se—, and, most preferably, —S—.

$R_2$ to $R_5$ defined as alkyl-$(Z_1)_n$—are preferably $C_1$-$C_{12}$-alkyl-$(Z_1)_n$—, more particularly $C_1$-$C_8$alkyl-$(Z_1)$-$n$, more particularly $C_1$-$C_8$alkyl-$(Z_1)$-$n$ and, most preferably, $C_1$-$C_4$alkyl-$(Z_1)$-$n$. Alkyl is preferably linear alkyl. Exemplary alkyl groups are methyl, ethyl, n- and isopropyl, n-, iso- and tert-butyl, pentyl, hexyl, heptyl, octyl, nonyl, decyl, undecyl, dodecyl, tetradecyl, hexadecyl and octadecyl.

Methyl, ethyl, n- and isopropyl, n-, iso- and tert-butyl are especially preferred.

In a preferred embodiment of the invention, the group alkyl—$(Z_1)_n$—is methyl, ethyl, n- and isopropyl, n-, iso- and tert-butyl, methylthio, methylseleno, ethylthio and ethylseleno.

The $C_1$-$C_4$alkyl, $C_1$-$C_4$alkoxy and $C_1$-$C_4$alkylthio substituents may typically be methyl, ethyl, n- and isopropyl, n-, iso- and tert-butyl as well as corresponding alkoxy and alkylthio radicals. Preferred substituents are methyl, ethyl, n- and isopropyl, n- and isobutyl, methoxy, ethoxy, methylthio and ethylthio.

Typical examples of the phenyl—$(Z_1)_n$—or benzyl—$(Z_1)_n$—groups are phenyl, benzyl, phenylthio, phenylseleno, benzylthio, benzylseleno, methylphenyl, methylbenzyl, ethylphenyl, n- or isopropylphenyl, n-, iso- or tert-butylphenyl, dimethylphenyl, dimethylbenzyl, methoxyphenyl, methylthiophenyl, methylthiobenzyl, methylphenylthio and methylphenylseleno.

In formula IIIa $R_6$ is preferably H or $C_1$-$C_4$alkyl. The most preferred meaning of $R_6$ is H, methyl or ethyl.

Z in formula IIIa is preferably —S— or —NR$_7$—and, most preferably, —NR$_7$—. $R_7$ is preferably H or $C_1$-$C_4$alkyl, and is most preferably H, methyl or ethyl.

$Z_1$ is preferably —S—and $Z_2$ is preferably —O—or —S—.

A preferred subgroup of the compounds of formula I comprises those compounds wherein in formula II R is H, methyl or ethyl and is most preferably H, $R_1$ is H or methyl and most preferably H, and $X_1$ to $X_4$ is =N—CN, and, in formulae III and IIIa, $R_2$ and $R_3$ as well as $R_4$ and $R_5$ or $R_2$ to $R_5$ are identical and are H, linear or branched $C_1$-$C_8$alkyl—$(Z_1)$ $_n$—, unsubstituted or $C_1$-$C_4$alkyl-substituted phenyl—$(Z_1)_n$—or benzyl—$(Z_1)_n$—, or $R_2$ and $R_3$ and $R_4$ and $R_5$ are each together independently of the other unsubstituted or $C_1$-$C_4$alkyl-substituted trimethylene, tetramethylene, —$Z_2$—$(CH_2)$—$Z_2$—, —$Z_2$—$(CH_2)$—/$Z_2$—, —$Z_2$—$(CH_2)_2$—$Z_2$—, —$Z_1$—CH=CH—$Z_1$—or —CH=CH—CH=CH—, n is 0 or 1, $Y_1$ and $Y_2$ are —S—, $Z_1$ is —S—, $Z_2$ is —O—or —S—, Z is —S—or NR$_7$, and $R_7$ is H or $C_1$-$C_4$alkyl, and $R_6$ is H or $C_1$-$C_4$alkyl.

A particularly preferred subgroup of the compounds of formula I comprises those compounds wherein, in formula II, R and $R_1$ are H, $X_1$ to $X_4$ are =N—CN, and in formulae III and IIIa $R_2$ to $R_5$ are identical and are H, or are linear or branched $C_1$-$C_4$alkyl—$(Z_1)_n$—, or $R_2$ and $R_3$ as well as $R_4$ and $R_5$ are each together trimethylene, tetramethylene, —$Z_2$—$(CH_2)$—$Z_2$—, —$Z_2$—$(CH_2)_2$—$Z_2$—, —$Z_1$—CH=CH—$Z_1$ or —CH=CH—CH=CH—, n is 0 or 1, $Y_1$ and $Y_2$ are —S—, $Z_1$ is —S—, $Z_2$ —O—or —S—, Z is —S—or NR$_7$, and $R_7$ is H or $C_1$-$C_4$alkyl, and $R_6$ is H or $C_1$-$C_4$alkyl.

In a particularly preferred embodiment of the invention, the novel compositions contain those compounds of formula I, wherein A is 5,7,12,14-pentacenetetracyanoimine and B is a compound of formula IIIb

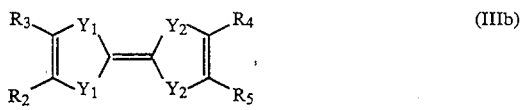

wherein $Y_1$ and $Y_2$ are each —S—, and $R_2$, $R_3$, $R_4$ and $R_5$ are each independently of one another H, $C_1$-$C_4$alkyl or $C_1$-$C_4$alkylthio or $R_2$ and $R_3$ as well as $R_4$ and $R_5$ when taken together, are each —S—CH$_2$CH$_2$—S—. Preferably $R_2$ and $R_3$ and $R_4$ and $R_5$ in formula IIIb are identical radicals and, most preferably, $R_2$ to $R_5$ are identical radicals.

Illustrative examples of CT complexes of formula I are those wherein A in formula I is 5,7,12, 14-pentacenetetracyanoimine, and B is tetrathiofulvalene, tetramethyltetrathiofulvalene, tetramethyltetrathiofulvalene, dimethyldiethyltetrathiofulvalene, tetra-n-propyltetrathiofulvalene, tetra-n-butyltetrathiofulvalene, tetra(methylthio)tetrathiofulvalene, tetra(ethylthio)tetrathiofulvalene, tetra(n-propylthio)tetrathiofulvalene, tetra(n-butylthio)tetrathiofulvalene, dimethyldimethylthiotetrathiofulvalene, diethyldimethylthiotetrathiofulvalene, diethylthiodimethylthiotetrathiofulvalene and tetraselenofulvalene.

In another of its aspects, the invention relates to a process for the preparation of CT complexes of formula I, which comprises reacting equimolar amounts of a fulvalene derivative B and a pentacenecyanoimine of formula II in an inert organic solvent. Equimolar amounts means that about 1 equivalent of the fulvalene derivative of formula III or IIIa is reacted with about 1 equivalent of the pentacenecyanoimine of formula II to form the 1:1 complexes.

The fulvalene derivatives are known, some are commercially available or they can be prepared by known standard methods. The preparation of 5,7,12,14-pentacenetetracyanoimine is described by L. L. Miller in Synthetic Metals, 41–43, pages 2365–2375 (1991). The starting unsubstituted or substituted 5,7,12,14-pentacenetetrones are obtainable by a process described by W. H. Mills et. al. in J. Chem. Soc. 101, page 2194 (1912). The 5,7,12,14-pentacenetetracyanoimines can be purified by conventional methods, conveniently by recrystallization or chromatographic methods. If no special protective measures are taken, for example anhydrous conditions, cyanoimine groups can be replaced by oxygen, but without adversely affecting the formation of the desired CT complexes.

The inventive process is conveniently carded out at elevated temperature, typically at 30°-200° C., preferably at 50°-100° C.

Suitable solvents are typically non-polar, polar and aprotic solvents which may be used singly or in mixtures of at least two solvents. Typical examples are: ethers (dibutyl ether, tetrahydrofuran, dioxane, ethylene glycol monomethyl or dimethyl ether, ethylene glycol monoethyl or diethyl ether, diethylene glycol diethyl ether, triethylene glycol dimethyl ether), halogenated hydrocarbons (methylene chloride, chloroform, 1,2-dichlorethane, 1,1,1-trichloroethane, 1,1,2,2-tetrachloroethane), carboxylates and lactones (ethyl acetate, methyl propionate, ethyl benzoate, 2-methoxyethylacetate, γ-butyrolactone, δ-valerolactone, pivalolactone), carboxamides and lactams (N,N-dimethylformamide, N,N-diethylformamide, N,N-dimethylacetamide, tetramethylurea, hexamethylphosphoric triamide, γ-butyrolactam, ε-caprolactam, N-methylpyrrolidone, N-acetylpyrrolidone, N-methylcaprolactam), sulfoxides (dimethyl sulfoxide), sulfones (dimethyl sulfone, diethyl sulfone, timethylene sulfone, tetramethylene sulfone), tertiary amines (N-methylpiperidine, N-methylmorpholine), substituted benzenes (benzonitrile, chlorobenzene, o-dichlorobenzene, 1,2,4-trichlorobenzene, nitrobenzene, toluene, xylene), nitriles (acetoniuile, propionitrile) and aliphatic or cycloaliphatic hydrocarbons (petroleum ether, pentane, hexane, cyclohexane and methylcyclohexane). Suitable solvents are also aromatic-aliphatic ethers, for example methyl or ethyl phenyl ether, and ketones such as acetone, methyl ethyl ketone, methyl propyl ketone, dipropyl ketone, dibutyl ketone and methyl isobutyl ketone.

The CT complexes obtainable by the process of this invention are obtained in great purity and, after filtration, need only be washed with solvents. Ordinarily they are obtained as dark coloured to black needle-shaped crystals which have conductivities of more than 0.1 S/cm. They therefore have excellent suitability for use as electric conductors. Depending on the type of CT complex and on the amount added it is possible to obtain electrically conductive or antistatically treated polymers by incorporating these CT complexes in polymer materials, the CT complex being present in the polymer matrix as a network of crystal needles. Depending on the concentration of CT complex in the polymer matrix, very fine meshed needle networks can be obtained.

In yet another of its aspects, the invention relates to CT complexes of formula Ia $$[A]^{\ominus} \cdot B^{\oplus} \quad (Ia),$$

wherein A is a compound of formula II or a mixture of compounds of formula II,

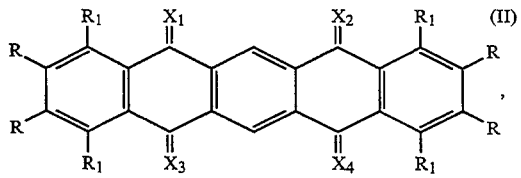

wherein the R substituents are identical and are H or $C_1$-$C_4$alkyl, or the adjacent R substituents, taken together, are —(CH$_2$)$_3$—or—(CH$_2$)$_4$—; $R_1$ is H or $C_1$-$C_4$alkyl; and $X_1$ is =N—CN, and $X_2$, $X_3$ and $X_4$ are each independently of one another =O or =N—CN, and B is a compound of formula III or IIIa

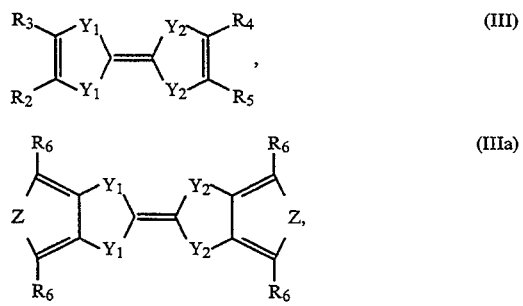

wherein $R_2$, $R_3$, $R_4$ and $R_5$ are each independently of one another H, linear or branched $C_1$-$C_{18}$alkyl—($Z_1$-)$_n$—, phenyl—($Z_1$)$_n$—or benzyl—($Z_1$)$_n$—which are unsubstituted or substituted by $C_1$-$C_4$alkyl, $C_1$-$C_4$alkoxy or $C_1$-$C_4$alkylthio, or $R_2$ and $R_3$ as well as $R_4$ and $R_5$ are each independently of the other trimethylene, tetramethylene, —$Z_2$—(CH$_2$)—$Z_2$—, —$Z_2$—(CH$_2$)$_2$—$Z_2$—, —$Z_1$—CH=CH—$Z_1$—or —CH=CH—CH=CH—, each unsubstituted or substituted by $C_1$-$C_4$alkyl, $C_1$-$C_4$alkoxy or $C_1$-$C_4$alkylthio, n is 0 or 1 steht, $Y_1$ and $Y_2$ are each independently of the other —S—or —Se—, $Z_1$ is —S—or —Se—, $Z_2$ is —O—, —S—or —Se—, Z is —S—, —Se—or $NR_7$, and $R_7$ is H, $C_1$-$C_6$alkyl, phenyl or benzyl, and $R_6$ is H, $C_1$-$C_4$alkyl, phenyl or benzyl, with the exception of [(5,7,12,14-tetracenetetracyanoimine)(tetrahiofulvalene)].

In yet another of its aspects, the invention relates to CT complexes of formula I with the exception of [(5,7,12,14-tetracenetetracyanoimine)(tetrathiofulvalene)] in the form of needle-shaped crystals.

In respect of the novel CT complexes of formula I, the same preferences and exemplary embodiments apply as cited previously with respect to the CT complexes in the novel compositions.

The novel compositions may contain the CT complex in a concentration of 0.01 to 30 % by weight, preferably of 0.01 to 20 % by weight, more particularly of 0.01 to 10 % by weight and, most preferably, of 0.1 to 5 % by weight, based on said composition.

The thermoplastic polymers may conveniently be selected from among the following polymers, copolymers or mixtures of these polymers:

1. Polymers of monoolefins and diolefins, for example polypropylene, polyisobutylene, polybut-1-ene, polymethylpent-1-ene, polyisoprene or polybutadiene, as well as polymers of cycloolefins, for example of cyclopentene or norbomene, polyethylene (which can be uncrosslinked or crosslinked), for example high density polyethylene (HDPE), low density polyethylene (LDPE), linear low density polyethylene (LLDPE), branched low density polyethylene (BLDPE).

2. Mixtures of the polymers mentioned under 1 ), for example mixtures of polypropylene with polyisobutylene, polypropylene with polyethylene (for example PP/HDPE, PP/LDPE) and mixtures of different types of polyethylene (for example LDPF/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, ethylene/hexene copolymers, ethylene/ethylpentene copolymers, ethylene/heptene copolymers, ethylene/octene copolymers, propylene/isobutylene copolymers, ethylene/but-1-ene copolymers, propylene/butadiene copolymers, isobutylene/isoprene copolymers, ethylene/alkyl acrylate copolymers, ethylene/allcyl methacrylate copolymers, ethylene/vinyl acetate or ethylene/acrylic acid copolymers and the salts thereof (ionomers), as well as terpolymers of ethylene with propylene and a diene, such as hexadiene, dicyclopentadiene or ethylidene-norbornene; and also mixtures of such polymers with one another and with polymers mentioned in 1 ) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

3a. Hydrocarbon resins (for example C5–C9)including hydrogenated modifications thereof (for example tackifiers) and mixtures of polyalkylenes and starch.

4. Polystyrene, poly(p-methylstyrene), poly(α-methylstyrene).

5. Copolymers of styrene or α-methylstyrene with dienes or acrylic derivatives, for example styrene/butadiene, styrene/acrylonitrile, styrene/alkyl methacrylate, styrene/maleic anhydride, styrene/butadiene/alkyl acrylate, styrene/butadiene/alkyl methacrylate styrene/acrylonitrile/methyl acrylate; mixtures of high impact strength from styrene copolymers and another polymer, for example from a polyacrylate, a diene polymer or an ethylene/propylene/diene terpolymer; and block copolymers of styrene, for example styrene/butadiene/styrene, styrene/isoprene/styrene, styrene/ethylene/butylene/-styrene or styrene/ethylene/propylene/styrene.

6. Graft copolymers of styrene or α-methylstyrene, for example styrene on polybutadiene, styrene on polybutadiene-styrene or polybutadiene-acrylonitrile copolymers; styrene and acrylonitrile (or methacrylonitrile) on polybutadiene; styrene and maleic anhydride or maleimide on polybutadiene; styrene, acrylonitrile and maleic anhydride or maleimide on polybutadiene; styrene, acrylonitrile and methyl methacrylate on polybutadiene, styrene and alkyl acrylates or methacrylates on polybutadiene, styrene and acrylonitrile on ethylene/propylene/diene terpolymers, styrene and acrylonitrile on polyacrylates or polymethacrylates, styrene and acrylonitrile on acrylate/butadiene copolymers, as well as mixtures thereof with the copolymers listed in 5), for example the copolymer mixtures known as ABS, MBS, ASA or AES polymers.

7. Halogen-containing polymers, such as polychloroprene, chlorinated rubbers, chlorinated or chlorosulfonated polyethylene, copolymers of ethylene and chlorinated ethylene, epichlorohydrin homo- and copolymers, polymers of halogenated vinyl compounds, for example polyvinyl chloride, polyvinylidene chloride, polyvinyl fluoride, polyvinylidene fluoride, as well as copolymers thereof, for example vinyl chloride/vinylidene chloride, vinyl chloride/vinyl acetate or vinylidene chloride/vinyl acetate copolymers.

8. Polymers derived from α,β-unsaturated acids and derivatives thereof, such as polyacrylates and polymethacrylates, polymethyl methacrylate impact-modified with butyl acrylate, polyacrylamides and polyacrylonitrile.

9. Copolymers of the monomers mentioned in 8) with each other or with other unsaturated monomers, for example acrylonitrile/butadiene, acrylonitrile/alkyl acrylate, acrylonitrile/alkoxyalkyl acrylate or acrylonitrile/vinyl halide copolymers or acrylonitrile/alkyl methacrylate/butadiene terpolymers.

10. Polymers derived from unsaturated alcohols and amines, or acyl derivatives thereof or acetals thereof, such as polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.

11. Homopolymers and copolymers of cyclic ethers, such as polyalkylene glycols, polyethylene oxide, polypropylene oxide or copolymers thereof with bis(glycidyl) ethers.

12. Polyacetals such as polyoxymethylene and those polyoxymethylenes which contain ethylene oxide as a comonomer, polyacetals modified with thermoplastic polyurethanes, acrylates or MBS.

13. Polyphenylene oxides and sulfides and mixtures thereof with styrene polymers or polyamides.

14. Polyurethanes derived from polyethers, polyesters or hydroxyl-terminated polybutadienes on the one hand and aliphatic or aromatic polyisocyanates on the other, as well as precursors thereof.

15. Polyamides and copolyamides derived from diamines and dicarboxylic acids and/or from aminocarboxylic acids or the corresponding lactams, such as polyamide 4, polyamide 6, polyamide 6/6, 6/10, 6/9, 6/12, 4/6, 12/12, polyamide 11, polyamide 12, aromatic polyamides obtained by condensation of m-xylene dianfine and adipic acid; polyamides prepared from hexamethylenediamine and isophthalic or/and terephthalic acid and optionally an elastomer as modifier, for example poly-2,4,4,-trimethylhexamethylene terephthalamide or poly-m-phenylene isophthalamide; and also copolymers of the aforementioned polyamides with polyolefins, olefin copolymers, ionomers or chemically bonded or grafted elastomers; or with polyethers, as with polyethylene glycols, polypropylene glycols or polytetramethylene glycols; polyamides or copolyamides modified with EPDM or ABS; polyamides condensed during processing (RIM polyamide systems).

16. Polyureas, polyimides, polyamide-imides and polybenzimidazoles.

17. Polyesters derived from dicarboxylic acids and diols and/or from hydroxycarboxylic acids or the corresponding lactones, such as polyethylene terephthalate, polybutylene terephthalate, poly-1,4-dimethylolcyclohexane terephthalate, poly[2,2,-(4-hydroxyphenyl)-propane] terephthalate and polyhydroxybenzoates as well as block copolyether esters derived from hydroxyl-terminated polyethers; and also polyester modified with polycarbonates or MBS.

18. Polycarbonates and polyester carbonates.

19. Polysulfones, polyether sulfones and polyether ketones.

20. Polyethers of digylcidyl compounds, typically diglycidyl ethers and diols, e.g. of the diglycidyl ether of bisphenol A and bisphenol A.

21. Natural polymers, such as cellulose, rubber, gelatin and chemically modified homologous derivatives thereof, such as cellulose acetates, cellulose propionates and cellulose butyrates, or the cellulose ethers such as methyl cellulose; as well as rosins and their derivatives.

22. Blends of the aforementioned polymers (polyblends), for example PP/EPDM, polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPE/HIPS, PPE/PA 66 and copolymers, PA/HDPE, PA/PP, PA/PPO, PC/poly(epichlorohydrin).

Preferred thermoplastic polymers are polyolefins, polystyrene, polyvinyl chloride, polyvinylidene chloride, polyvinylidene fluoride, polyacrylates, polymethacrylates, polyamides, polyesters, polycarbonates, aromatic polysulfones, aromatic polyethers, aromatic polyether sulfones, polyimides and polyvinyl carbazole.

The thermosetting and structurally crosslinked polymers may be typically the following polymers:

1. Crosslinked polymers which are derived from aldehydes on the one hand and phenols, ureas and melamines on the other hand, such as phenol/formaldehyde resins, urea/formaldehyde resins and melamine/formaldehyde resins.

2. Drying and non-drying alkyl resins.

3. Unsaturated polyester resins which are derived from copolyesters of saturated and unsaturated dicarboxylic acids with polyhydric alcohols and vinyl compounds as crosslinking agents, and also halogen-containing modifications thereof of low flammability.

4. Crosslinkable acrylic resins derived from substituted acrylic esters such as epoxy acrylates, urethane acrylates or polyester acrylates.

5. Alkyl resins, polyester resins or acrylate resins which are cross-linked with melamine resins, urea resins, polyisocyanates or epoxy resins.

6. Rubber derived from crosslinked polydienes, for example butadiene or isoprene; silicon rubber.

7. Epoxy resins which are derived from polyepoxides, for example from bisglycidyl ethers or from cycloaliphatic diepoxides, and which may contain a hardener as crosslinking agent or which are crosslinked thermally using curing accelerators or by irradiation.

Among the crosslinked polymers, crosslinked epoxy resins are preferred which, as polyepoxides, are derived preferably from glycidyl compounds which contain on average two epoxy groups in the molecule. Particularly suitable glycidyl compounds are those which contain two glycidyl groups, $\beta$-methylglycidyl groups or 2,3-epoxycyelopentyl groups attached to a hetero atom (e.g. sulfur, preferably oxygen or nitrogen), in particular bis(2,3-epoxycyclopentyl) ether; diglycidyl ethers of polyhydric aliphatic alcohols, such as 1,4-butanediol, or polyalkylene glycols, such as polypropylene glycols; diglycidyl ethers of cycloaliphatic polyols, such as 2,2-bis(4-hydroxycyclohexyl)propane; diglycidyl ethers of polyhydric phenols, such as resorcinol, bis(p-hydroxyphenyl)methane, 2,2-bis-(p-hydroxyphenyl)propane (=diomethane), 2,2-bis(4'-hydroxy-3'5'-dibromophenyl)propane, 1,3-bis(p-hydroxyphenyl)ethane; bis($\beta$-methylglycidyl) ethers of the above dihydric alcohols or dihydric phenols; diglycidyl esters of dicarboxylic acids, such as phthalic acid, terephthalic acid, $\Delta_4$-tetrahydrophthalic acid and hexahydrophthalic acid; N,N-diglycidyl derivatives of primary amines and amides and heterocyclic nitrogen bases which contain two N-atoms, and N,N'-diglycidyl derivatives of disecundary diamides and diamines, such as N,N-diglycidylaniline, N,N-diglycidyltoluidine, N,N-diglycidyl-p-aminophenyl methyl ether, N,N'-dimethyl-N,N'-diglycidylbis(p-aminophenyl)methane; N',N''-diglycidyl-N-phenyl-isocyanurate; N,N'-diglycidyl ethyleneurea; N,N'-diglycidyl-5,5-dimethylhydantoin, N,N'-diglycidyl-5-isopropyl-hydantoin, N,N-methylenebis-(N',N'-diglycidyl-5,5-dimethylhydantoin), 1,3-bis(N-glycidyl-5,5-dimethylhydantoin)-2-hydroxypropane; N,N'-diglycidyl-5,5-dimethyl-6-isopropyl-5,6-dihydrouracil, triglycidyl isocyanurate.

A preferred group of epoxy resins comprises glycidylated novolaks, hydantoins, aminophenols, bisphenols and aromatic dianfines or cycloaliphatic epoxy compounds. Particularly preferred epoxy resins are glycidylated cresol novolaks, bisphenol A and bisphenol F diglycidyl ether, hydantoin-N,N'-bisglycide, p-aminophenol triglycide, diaminodiphenylmethane tetraglycide, vinylcyclohexene dioxide, 3,4-epoxycyclohexylmethyl-3,4-epoxycyclohexanecarboxylate or mixtures thereof.

Further suitable epoxy resins are prereacted adducts of such epoxy compounds with epoxy hardeners, for example an adduct of bisphenol A diglycidyl ether and bisphenol A, or adducts which have been prereacted with oligoesters which carry two terminal carboxyl groups and epoxides.

Suitable hardeners for epoxy resins are acid or basic compounds. Illustrative examples of suitable hardeners are: polyhydric phenols (resorcinol, 2,2-bis(4-hydroxyphenyl)propane) or phenol-formaldehyde resins; polybasic carboxylic acids and the anhydrides thereof, such as phthalic anhydride, tetrahydrophthalic anhydride, hexahydrophthalic arthydride, 4-methylhexahydrophthalic anhydride, 3,6-endomethhylene-tetrahydrophthalic anhydride, 4-methyl-3,6-endomethylen-tetrahydrophthalic anhydride (methylnadic anhydride), 3,4,5,6,7,7-hexachloroendomethylene-tetrahydrophthalic anhydride, succinic anhydride, adipic anhydride, trimethyladipic anhydride, sebacic anhydride, maleic anhydride, dodecylsuccinic anhydride, pyromellitic dianhydride, trimellitic anhydride, benzophenonetetracarboxylic dianhydride, or mixtures of such anhydrides.

A preferred group of hardeners comprises novolaks and polycarboxylic anhydrides.

The epoxy resins can also be additionally cured with curing accelerators or only with thermal curing catalysts. Exemplary of curing accelerators and catalysts are 3-ethyl-4methylimidazole, triamylamrnonium phenolate; mono- or polyphenols (phenol, diomethane, salicylic acid); boron trifluoride and the complexes thereof with organic compounds, such as boron trifluoride ether complexes and boron trifluoride amine complexes (BF$_3$/monoethylamine complex); phosphoric acid and triphenylphosphite.

Curing accelerators and catalysts are normally added in an amount of 0.1 to 10 % by weight, based on the epoxy resin. Hardeners for epoxy resins are normally used in equimolar amounts, based on the epoxy groups and functional groups of a hardener.

Further additives for enhancing processing properties, the mechanical, electrical and thermal properties, surface properties and light stability can be blended into the novel formulation. Exemplary of such additives are finely particulate fillers, reinforcing fillers, plasticisers, lubricants and mould release agents, adhesion promoters, antistatic agents, antioxidants, heat and light stabilizers, pigments and dyes.

In a preferred embodiment of the invention, the novel compositions are shaped to mouldings, films, foils, fibers, or to coatings on at least one surface of a substrate.

In yet another of its aspects, the invention relates to a process for the preparation of novel compositions, which comprises (a) blending a CT complex of formula I into a thermoplastic polymer, (b) blending a CT complex of formula I with at least one component of a thermosetting or structurally crosslinkable polymer and then polymerizing the blend, together with a further optional component, to a thermosetting or structurally crosslinked polymer, or (c) dissolving a compound of formula II or a fulvalene derivative of formula III or IIIa, together with a thermoplastic polymer or with at least one component of a thermosetting or structurally crosslinkable polymer in an organic solvent, mixing this solution, together with further optional components of a thermosetting or structurally crosslinkable polymer with a solution of a fulvalene derivative of formula 1/I or IIIa or a compound of formula II, removing the solvent and polymerizing curable mixtures to a thermosetting or structurally crosslinked polymer. The process can be combined with a shaping process.

The preparation of the novel compositions can be carried out by methods known in plastics technology. In shaping techniques for polymers, typically casting, compression moulding, injection moulding and extrusion, the CT complex itself can be added to a thermoplastic polymer or to at least one component of a thermosetting plastic to form a suspension, or separately to each component (e.g. the epoxy resin and the hardener) to form a solution or suspension, such that after shaping the CT complex crystallises and precipitates in the form of needles during cooling and the needless form a network in a polymer matrix.

In a particularly preferred embodiment of the invention, the novel composition is in the form of a film or foil or a coating on at least one surface of a substrate. Such embodiments are conveniently prepared by suspending and/or dissolving a thermoplastic polymer or at least one starting material of a thermosetting polymer or a structurally crosslinked polymer in an inert solvent together with a CT complex of formula I, or dissolving a thermoplastic polymer or at least one starting material of a thermosetting polymer or a structurally crosslinked polymer together with a compound of formula II or a fulvalene derivative B, and then mixing the solution or suspension with a solution of the fulvalene derivative B or a compound of formula II, and subsequently applying the mixture by known coating techniques to a substrate which may be preheated, and thereafter removing the solvent by heating, such that crosslinkable mixtures can then be fully cured. Self-supporting films and foils are obtained by peeling the coating from the substrate or by extrusion.

Examples of suitable substrates are glass, metals, plastics, mineral and ceramic materials, wood and paper. The substrates may be of any external shape and are typically mouldings, filaments, fibers, fabrics, bars, pipes, ribbons, sheets, boards, rolls or casings.

Suitable coating techniques are typically brushing, rolling, doctor coating, casting, spin coating, curtain coating and spraying. Spraying methods are especially preferred, as on the one hand very thin and uniform layers with substantially isotropic, very fine-mesh and homogeneous networks are obtainable from crystal needles of the CT complexes and, on the other, the size of the crystal needles and the mesh width of the networks can be controlled by the droplet size, even when suspensions are sprayed.

Suitable inert solvents for polymers and starting materials for polymers are typically polar and, preferably, aprotic solvents, which may be used singly or in mixtures of at least two solvents. Representative examples of such solvents are: ethers (dibutyl ether, tetrahydrofuran, dioxane, ethylene glycol monomethyl or dimethyl ether, ethylene glycol monoethyl or diethyl ether, diethylene glycol diethyl ether, triethylene glycol dimethyl ether), halogenated hydrocarbons (methylene chloride, chloroform, 1,2-dichloroethane, 1,1,1-trichloroethane, 1,1,2,2-tetrachloroethane), carboxylates and lactones (ethyl acetate, methyl propionate, ethyl benzoate, 2-methoxyphenyl acetate, γ-butyrolactone, δ-valerolactone, pivalolactone), carboxamides and lactams (N,N-dimethylformamide, N,N-diethylformamide, N,N-dimethylacetamide, tetramethylurea, hexamethylphosphofic triamide, γ-butyrolactam, ε-caprolactam, N-methylpyrrolidone, N-acetylpyrrolidone, N-methylcaprolactam), sulfoxides (dimethyl sulfoxide), sulfones (dimethyl sulfone, diethyl sulfone, trimethylene sulfone, tetramethylene sulfone), tertiary amines (N-methylpiperidine, N-methylmorpholine) substituted benzenes (benzonitrile, chlorobenzene, o-dichlorobenzene, 1,2,4-trichlorobenzene, nitrobenzene, toluene, xylene) and nitriles (acetonitrile, propionitrile). Further suitable solvents are aromatic-aliphatic ethers such as methyl or ethyl phenyl ether as well as ketones such as acetone, methyl ethyl ketone, methyl propyl ketone, methyl butyl ketone, dipropyl ketone, dibutyl ketone and methyl isobutyl ketone. Suitable solvents for the compounds of formula II and the fulvalene derivatives B have been mentioned hereinabove.

The coating techniques can conveniently be carried out by dissolving the individual components separately and combining them just before application of the chosen technique. However, it is also possible to prepare two solutions of the components, for example of polymer solution and fulvalene derivative B or of a compound of formula II, and solution of a compound of formula II or of a fulvalene derivative B together with a polymer, or to combine all the components in one solution. In this last mentioned case, the CT complexes can crystallise out already prior to coating; but this has virtually no effect on the desired quality of the coating.

The solutions are preferably heated, conveniently to 30°–200° C. It is useful to heat the substrate as well to accelerate the removal of the solvent, which is normally effected in temperature range from 50° to 150° C., preferably 50° to 100° C., until the coating is dry. If it is desired to detach the coatings to give self-supporting films or sheets, the substrate can be treated with antiblocking agents prior to coating.

An alternative coating method comprises suspending the CT complexes, which are obtained as needle-shaped crystals, in a solution of a polymer or of starting materials for thermosetting polymers, then coating a substrate and afterwards removing the solvent, and, if appropriate, thereafter effecting a cure to form the thermosetting polymers. It is also possible to prepare dry powder mixtures from polymer powders or solid starting materials for thermosetting polymers and the CT complexes, and to process these mixtures in coating or electrostatic coating methods to layers on substrates. Networks of crystal needless in a polymer matrix are also obtained in these alternative methods.

It is also possible to produce pure layers of networks of crystal needles of the CT complexes on a substrate by applying to a substrate solutions or suspensions of the CT complexes in a solvent and afterwards evaporating the solvent. Such layers can be electrochemically metallized to enhance the conductivity, conveniently with Cu, Pt or Pd. It can be useful to provide such pure layers with a protective coating of a polymer or to coat the pure layers subsequently with a polymer.

The layer thicknesses can vary over a wide range, depending on the choice of coating method. Spray methods give very thin layers, whereas thicker layers can also be obtained with brushing and casting methods. The layer thicknesses can be typically from 0.01 to 5000 μm, preferably from 0.1 to 1000 μm and, most preferably, from 0.1 to 500 μm.

Depending on the choice of polymer, the novel compositions are opaque or transparent and have outstanding electrical properties. Thus, surprisingly, the coatings and mouldlings have an excellent discharge capacity which, for heterogeneous materials, is otherwise difficult to achieve or cannot be achieved at all. The compositions are therefore especially suitable for use for making antistatically treated moulded pans for the electrostatic screening of components or for making antistatically treated mouldings. The high conductivities also permit the use of the novel compositions as electric conductors, for example as electrodes for display elements or electronic components as well as charge carriers in capacitors. The compositions also have excellent mechanical strength and performance properties. The compositions can also be prepared at comparatively low temperatures and have the additional advantage of causing no or only insignificant corrosion in metallic machine pans. Furthermore, they have good stability to the action of heat and/or moisture.

Further objects of the invention are the use of the novel charge transfer complexes of formula I as electric conductors; the use of the novel compositions as antistatically treated moulded pans for the electronic screening of components or as antistatically treated mouldings; the use of the novel compositions as electric conductors; the use of the novel compositions as electrode material; and the use of the novel compositions in the form of films or foils as charge carriers in capacitors.

The following Examples illustrate the invention in more detail.

A) PREPARATION OF THE CT COMPLEXES

Example A1: Preparation of a CT complex from tetrahiofulvalene and 5,7,12,14-pentacenetetracyanoimine A solution warmed to 80° C. of 200 mg (0.460 mmol) of 5,7,12,14-tetracenetetracyanoimine in 200 ml of 1,2-dichloroethane is added to a solution warmed to the same temperature of 94 mg (0.460 mmol) of tetrathiofulvalene in 10 ml of 1,2-dichloroethane. The resultant dark yellow suspension is first cooled to room temperature and then to −5° C. The precipitate is isolated by filtration, washed With $CH_2Cl_2$ and then dried under a high vacuum to give dark green crystal needless of the title compound in a yield of 197 mg (67 %). The pressed pellet conductivity is 19.0 S/cm. Elemental analysis found (calcd.): C 59.75 (60.17); H 2.35 (2.21); N 17.48 (17.54); S 19.80 (20.08). Decomposition temperature 256° C.

Example A2: Preparation of a CT complex from tetramethyltetrathiofulvalene and 5,7,12,14-pentacenetetracyanoimine A solution warmed to 80° C. of 130 mg (0.506 mmol) of tetramethyltetrathiofulvalene in 20 ml of 1,2-dichlorethane is added to a solution warmed to the same temperature of 217 mg (0.500 mmol) of 5,7,12,14-pentacenetetracyanoimine in 200 ml of 1,2-dichlorethane. The resultant dark yellow suspension is first cooled to room temperature and then to −5° C. The precipitate is isolated by filtration, washed with $CH_2Cl_2$ and then dried under a high vacuum to give dark red crystal needles of the title compound in a yield of 211 mg (61%). The pressed pellet conductivity is 9.0 S/cm. Elemental analysis found (calcd.): C 61.83 (61.23); H 3.12 (3.19); N 16.28 (16.13); S 18.05 (18.46). Decomposition temperature 226° C.

Example A3: Preparation of a CT complex from bis(dithioethylene)tetrahiofulvalene and 5,7,12,14-pentacenetetracyanoimine A solution warmed to 100° C. of 57 mg (0.13 mmol) of 5,7,12,14-pentacenetetracyanoimine in 30 ml of anisole is added to a solution warmed to the same temperature of 100 mg (0.260 mmol) of bis(dithioethylene)tetrathiofulvalene in 20 ml of anisole. The resultant red suspension is cooled to room temperature. The precipitate is isolated by filtration, washed with diethyl ether and then dried under a high vacuum to give black crystal needles of the title compound in a yield of 90 mg (57 %). The pressed pellet conductivity is $1.3 \times 10^{-2}$ S/cm. Elemental analysis found (calcd.): C 46.45 (45.90); H 2.50 (2.18); N 9.30 (9.31); S 42.43 (42.62).

Example A4: Preparation of a CT complex from tetraselenofulvalene and 5,7,12,14-pentacenetetracyanoimine A solution warmed to 100° C. of 111 mg (0.260 mmol) of 5,7,12,14-pentacenetetracyanoimine in 30 ml of anisole is added to a solution warmed to the same temperature of 100 mg (0.260 mmol) of tetraselenofulvalene in 20 ml of anisole. The resultant red solution is cooled to −5° C. The precipitate is isolated by filtration, washed with diethyl ether and then dried under a high vacuum to give 90 mg (57 %) dark red crystal needles of the title compound with a pressed pellet conductivity of 4.8 S/cm. Elemental analysis found (calcd.): C 46.90 (46.51); H 1.78 (1.71); N 13.56 (13.56); Se 37.80 (38.22).

B) USE EXAMPLES

Example B1:

A solution warmed to 70° C. of 4 mg of 5,7,12,14-pentacenetetracyanoimine in 3 ml of 1,2-dichloroethane is added to a solution warmed to the same temperature of mg of polycarbonate and 1.5 mg of tetrathiofulvalene in 3 ml of 1,2-dichloroethane. Aliquots of the mixture are poured on to a glass plate and the solvent is evaporated at different temperatures. The conductivity of the foils so obtained is measured.

| Evaporation temperature (°C.) | Conductivity (S/cm) |
|---|---|
| 40 | 0.03 |
| 45 | 0.14 |
| 50 | 0.03 |

What is claimed is:

1. A composition comprising a) a thermosetting, thermoplastic or structurally crosslinked polymer and b) a charge transfer complex of formula I in the form of a network of crystal needles in the polymer matrix

[A]⊖•B⊕ wherein A is a compound of formula II or a mixture of compounds of formula II

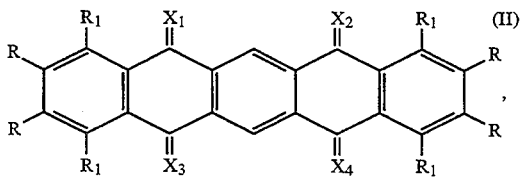

wherein the R substituents are identical and are H or $C_1$–$C_4$-alkyl, or the adjacent R substituents, taken together, are —$(CH_2)_3$—, or —$(CH_2)_4$—; $R_1$ is H or $C_1$–$C_4$alkyl; and $X_1$ is =N—CN, and $X_2$, $X_3$ and $X_4$ are =O or =N—CN, and B is a compound of formula III or IIIa

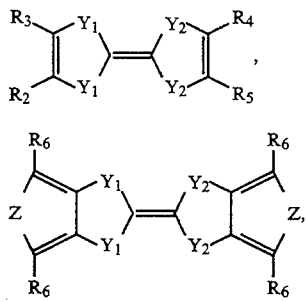

wherein $R_2$, $R_3$, $R_4$ and $R_5$ are each independently of one another H, linear or branched $C_1$-$C_{18}$alkyl—$(Z_1)_n$—, phenyl—$(Z_1)_n$— or benzyl—$(Z_1)_n$—which are unsubstituted or substituted by $C_1$-$C_4$alkyl, $C_1$-$C_4$alkoxy or $C_1$-$C_4$alkylthio, or $R_2$ and $R_3$ as well as $R_4$ and $R_5$ are together, each independently of the other trimethylene, tetramethylene, —$Z_2$—$(CH_2)$—$Z_2$—, —$Z_2$—$(CH_2)_2$—$Z_2$—, —$Z_1$—CH=CH—$Z_1$— or —CH=CH—CH=CH—, each unsubstituted or substituted by $C_1$-$C_4$alkyl, $C_1$-$C_4$alkoxy or $C_1$-$C_4$alkylthio, n is 0 is 1, $Y_1$ and $Y_2$ are each independently of the other —S— or —Se—, $Z_1$ is —S— or —Se—, $Z_2$ is —O—, —S— or —Se—, Z is —S—, —Se— or $NR_7$, and $R_7$ is H, $C_1$-$C_6$alkyl, phenyl or benzyl, and $R_6$ is H, $C_1$-$C_4$alkyl, phenyl or benzyl.

2. A composition according to claim 1, wherein the compounds of formulae III and IIIa have a reduction potential of less than or equal to 0.42 V, based on the standard calomel electrode.

3. A composition according to claim 1, wherein R in formula II is $C_1$-$C_4$alkyl and $R_1$ is H.

4. A composition according to claim 1, wherein R1 in formula II is $C_1$-$C_4$alkyl and R is H.

5. A composition according to claim 1, wherein R and $R_1$ in formula II are H, methyl or ethyl.

6. A composition according to claim 1, wherein in formula II $X_1$ and $X_4$ are =N—CN and $X_2$ and $X_3$ are =O or =N—CN, or $X_2$ and $X_3$ are =N—CN and $X_1$ and $X_4$ are =O or =N—CN.

7. A composition according to claim 1, wherein $X_1$, $X_2$, $X_3$ and $X_4$ in formula II are =N—CN.

8. A composition according to claim 1, wherein $R_2$ and $R_3$ as well as $R_4$ and $R_5$ in formula III are identical.

9. A composition according to claim 1, wherein $Y_1$ and $Y_2$ in formula III and IIIa are each —S—.

10. A composition according to claim 1, wherein $R_2$ to $R_5$ in formula III defined as alkyl—$(Z_1)_n$—are $C_1$-$C_{12}$alkyl—$(Z_1)_n$—, wherein $Z_1$ and n are as defined in claim 1.

11. A composition according to claim 1, wherein alkyl—$(Z_1)_n$—is methyl, ethyl, n- and isopropyl, n-, iso- and tert-butyl, methylthio, methylseleno, ethylthio and ethylseleno.

12. A composition according to claim 1, wherein $R_6$ in formula IIIa is H or $C_1$-$C_4$alkyl.

13. A composition according to claim 1, wherein $Z_1$ is —S—and $Z_2$ is —S—or —O—.

14. A composition according to claim 1, wherein the CT complex of formula I is one in which, in formula II, R is H, methyl or ethyl, $R_1$ is H or methyl and $X_1$ to $X_4$ are =N—CN, and, in formulae III and IIIa, $R_2$ and $R_3$ as well as $R_4$ and $R_5$ or $R_2$ to $R_5$ are identical and are H, linear or branched $C_1$-$C_8$alkyl—$(Z_1)_n$—, unsubstituted or $C_1$-$C_4$alkyl-substituted phenyl—$(Z_1)_n$—or benzyl—$(Z_1)_n$—, or $R_2$ and $R_3$ as well as $R_4$ and $R_5$ are together, each independently of the other, unsubstituted or $C_1$-$C_4$alkyl-substituted trimethylene, tetramethylene, —$Z_2$—$(CH_2)$—$Z_2$—, —$Z_2$—$(CH_2)_2$—$Z_2$—, —$Z_1$—CH=CH—$Z_1$—or —CH=CH—CH=CH—, n is 0 or 1, $Y_1$ and $Y_2$ are —S—, $Z_1$ is —S—, $Z_2$ is —O—or —S—, Z is —S—or $NR_7$, and $R_7$ is H or $C_1$-$C_4$alkyl, and $R_6$ is H or $C_1$-$C_4$alkyl.

15. A composition according to claim 14, wherein the CT complex of formula I is one in which, in formula II, R and $R_1$ are H, $X_1$ to $X_4$ are =N—CN, and in formulae III and IIIa $R_2$ to $R_5$ are identical and are H, or are linear or branched $C_1$-$C_4$alkyl—$(Z_1)_n$—, or $R_2$ and $R_3$ as well as $R_4$ and $R_5$ are each together trimethylene, tetramethylene, —$Z_2$—$(CH_2)$—$Z_2$—, —$Z_2$—$(CH_2)_2$—$Z_2$—, —$Z_1$—CH=CH—$Z_1$—or —CH=CH—CH=CH—, n is 0 or 1, $Y_1$ and $Y_2$ are —S—, $Z_1$ is —S—, $Z_2$ is —O—or —S—, Z is —S—or $NR_7$, and $R_7$ is H or $C_1$-$C_4$alkyl, and $R_6$ is H or $C_1$-$C_4$alkyl.

16. A composition according to claim 1, wherein the CT complexes of formula I are those ion which A is 5,7,12,14-pentacenetetracyanoimine and B is a compound of formula IIIb

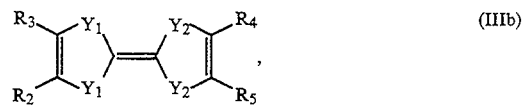

wherein $Y_1$ and $Y_2$ are each —S—, and $R_2$, $R_3$, $R_4$ and $R_5$ are each independently of one another H, $C_1$-$C_4$alkyl or $C_1$-$C_4$alkylthio or $R_2$ and $R_3$ as well as $R_4$ and $R_5$ together are —S—$CH_2CH_2$—S—.

17. A composition according to claim 16, wherein the CT complexes of formula I are those in which A in formula I is 5,7,12,14-pentacenetetracyanoimine, and B is selected from the group consisting of tetrathiofulvalene, tetramethyltetrathiofulvalene, tetramethyltetrathiofulvalene, dimethyldiethyltetrathiofulvalene, tetra-n-propyltetrathiofulvalene, tetra-n-butyltetrathiofulvalene, tetra(methylthio)tetrathiofulvalene, tetra(ethylthio)tetrathiofulvalene, tetra(n-propylthio)tetrathiofulvalene, tetra(n-butylthio)tetrathiofulvalene, dimethyldimethylthiotetrathiofulvalene, diethyldimethylthiotetrathiofulvalene, diethylthiodimethylthiotetrathiofulvalene and tetraselenofulvalene.

18. A composition according to claim 17, which contains the charge transfer complex in an amount of 0.01 to 30 % by weight, based on the weight of said composition.

19. A composition according to claim 17, which contains the charge transfer complex in an amount of 0.01 to 10 % by weight.

20. A composition according to claim 1, wherein the thermoplastic polymer is selected from the group consisting of polyolefins, polystyrene, polyvinyl chloride, polyvinylidene chloride, polyvinylidene fluoride, polyacrylates, polymethacrylates, polyamides, polyesters, polycarbonates, aromatic polysulfones, aromatic polyethers, aromatic polyether sulfones, polyimides and polyvinyl carbazole.

21. A composition according to claim 1, wherein the thermosetting polymer is an epoxy resin.

22. A composition according to claim 1 which is shaped to mouldings, films, toils, fibers or a coating on at least one surface of a substrate.

23. A composition according to claim 22, wherein the layer thickness of the coating is from 0.01 to 5000 μm.

24. A composition according to claim 23, wherein the layer thickness of the coating is from 0.1 to 1000 μm.

25. A composition according to claim 1, wherein R and $R_1$ are methyl or ethyl.

26. A composition according to claim 1, wherein R and $R_1$ are H.

27. A composition according to claim 1, wherein $R_2$, $R_3$, $R_4$ and $R_5$ are identical.

* * * * *